United States Patent

Jain et al.

[11] Patent Number: 5,400,800
[45] Date of Patent: Mar. 28, 1995

[54] DEVICE FOR MEASURING LUMBAR SPINAL MOVEMENT

[75] Inventors: Sanjeev Jain, Columbia; David A. Weiland, Baltimore, both of Md.

[73] Assignee: Baltimore Therapeutic Equipment Co., Hanover, Md.

[21] Appl. No.: 135,446

[22] Filed: Oct. 13, 1993

[51] Int. Cl.⁶ .............................................. A61B 5/103
[52] U.S. Cl. .................................................. 128/782
[58] Field of Search ................ 128/774, 781, 782; 33/511, 512

[56] References Cited

U.S. PATENT DOCUMENTS

| | | | |
|---|---|---|---|
| 4,708,148 | 11/1987 | Olson | 128/782 |
| 4,800,897 | 1/1989 | Nilsson | 128/782 |
| 5,042,505 | 8/1991 | Mayer et al. | 128/782 |
| 5,146,929 | 9/1992 | Sawhill | 128/751 |

FOREIGN PATENT DOCUMENTS 0494749  7/1992  European Pat. Off. ............ 128/782

*Primary Examiner*—Max Hindenburg
*Attorney, Agent, or Firm*—James J. Brown

[57] ABSTRACT

An improved device is described for measuring and registering lumbar spinal movement. The device, which is portable, is attached at an upper and lower portion of the lumbar region and measures multiple axis of motion by means of independent electric sensors. The device of the invention is an improvement over prior art devices because it provides appropriate compensation for errors induced through interaction of three axis only of rotational movement.

7 Claims, 8 Drawing Sheets

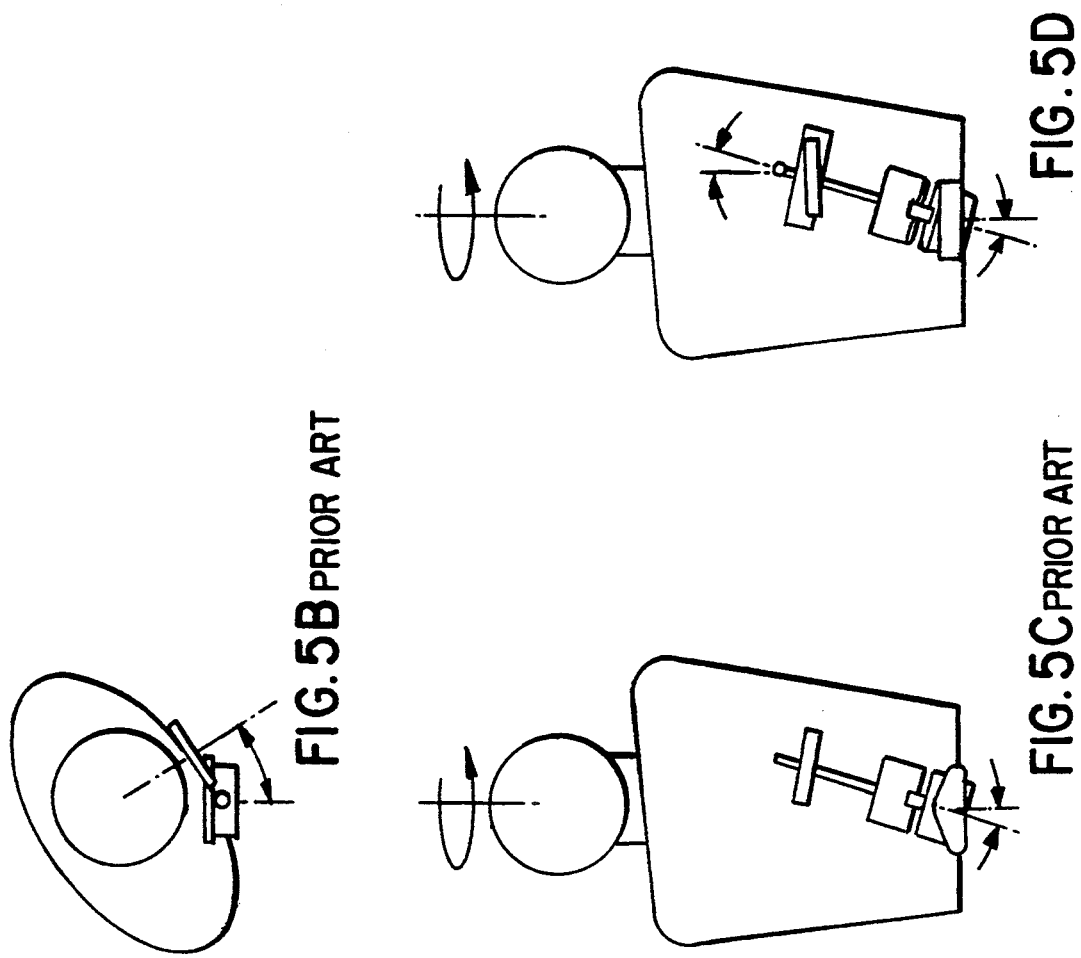
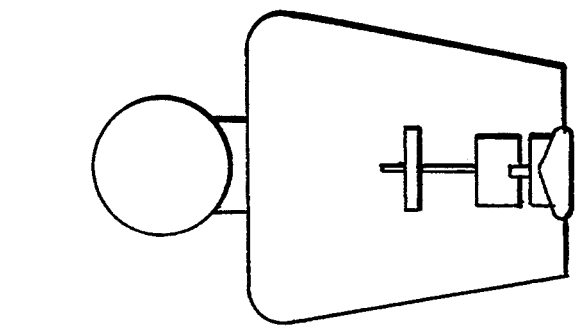

DEVICE FOR MEASURING LUMBAR SPINAL MOVEMENT

SUMMARY OF THE INVENTION

The present invention relates to a portable device that is used to measure movement of the lumbar region of the spine. More specifically the invention relates to a device which attaches to a human subject and quantitatively measures the three lumbar angles of movement: flexion/extension, lateral bending and rotation.

BACKGROUND OF THE INVENTION

Quantitative measurement of spinal motion in the lower back or lumbar region is vital in evaluating and treating physical impairment in this area, whether due to trauma, degenerative disease, or other causes. Because small inaccessible spinal joints do not readily lend themselves to the external visual observations typically required by standard goniometric measurement processes, such techniques for measuring spinal movement have been recognized to be highly inaccurate.

The mobility of spinal segments is confounded by motion above and below the points of measurement. The complexities involved in measuring spinal movement in the lumbar region have led to the development of large and cumbersome apparatuses which are not only expensive, but substantially reduce the ability of a subject to move normally during their use.

U.S. Pat. No. 5,146,929 to Sawhill, which is incorporated by reference herein, describes a device designed to provide a system for measuring the range of motion in the lumbar spinal region without use of visual techniques or cumbersome physical equipment that limits the activities of the subject.

While the device of the Sawhill patent is intended to measure all three lumbar angles of movement, it incorrectly assumes a relationship between the three axis of measurement which the device provides and actual lumbar movement. The resulting inaccurate determinations result from inadvertent motion of one axis of measurement caused by movement of one of the other axis. In other words, it has been found that the three axis of movement measured by the Sawhill device are not totally independent of one another and therefore cannot be used alone for accurately determining the corresponding three angles of Lumber motion.

It is accordingly an object of the present invention to provide an improved, portable device for quantitatively determining movement in the lumbar region of the spine which eliminates erroneous measurements resulting from mechanical coupling of the three axis of measurement associated with the three angles of lumbar movement.

It is a further object of the invention to provide an improved device for accurately determining lumber movement which compensates for inaccuracies in device of the prior art by providing for measurement of movement using additional sensors to calculate accurately the three lumbar angles of movement.

BRIEF DESCRIPTION OF THE DRAWINGS

FIG. 5 and FIGS. 5A-D compare the effects of mechanized coupling using the respective devices of FIG. 1 and 2.

DETAILED DESCRIPTION OF THE INVENTION

In accordance with the present invention a device is provided for accurately measuring the three angular movements of the lumbar spine by independently determining and correlating five independent axis of rotation associated with lumbar movement.

The device of the invention consists of an articulating enclosure consisting of two pivotally mounted housings, one of which is pivotally joined to a plate which attaches across the lower back of the subject. An elongated, rotatable shaft, which can telescope, pivotally connects the articulating enclosure with a third housing which attaches pivotally to a second plate which attaches also across the back of the subject at a higher location than the first plate. In all, five axis of rotation are provided at the respective pivot and rotation points, each of which is provided with a sensor for producing an electric signal in response to rotation about that axis. The five sets of independent electric signals resulting from the five rotational movements are transmitted to an appropriate register where they are correlated to provide an accurate determination of the three lumbar movements of the spine.

Figure 1:
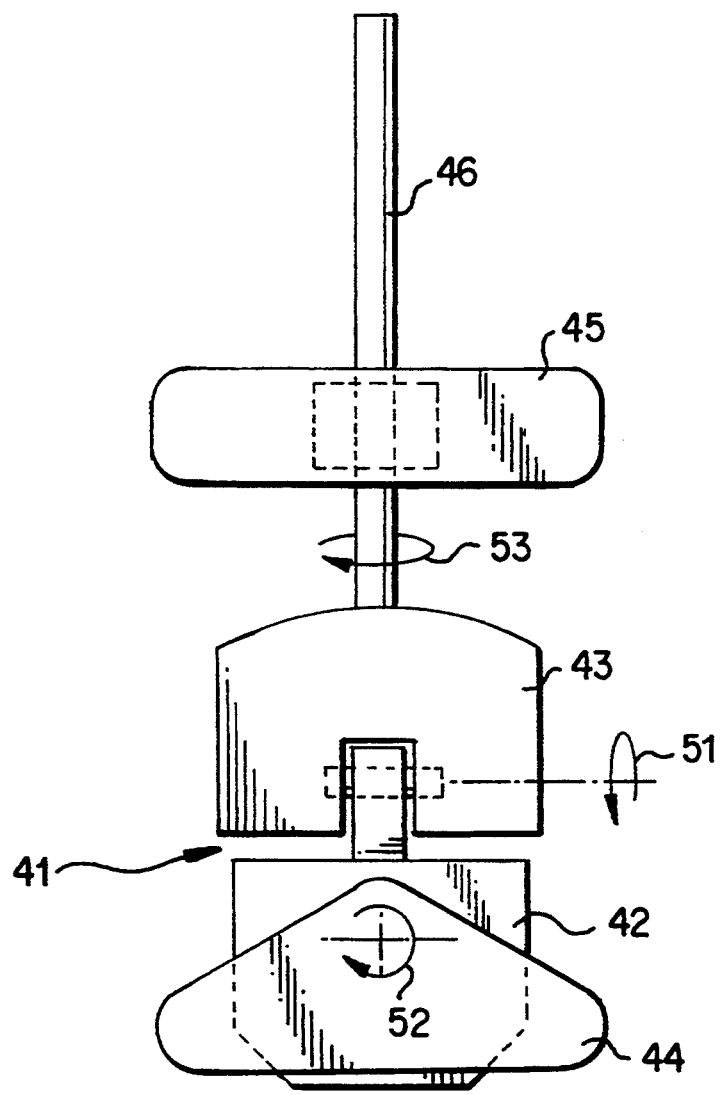
FIG. 1 is a depiction of the device of U.S. Pat. No. 5,146,929 showing the three axis of rotation measured by that device.
Figure 2:
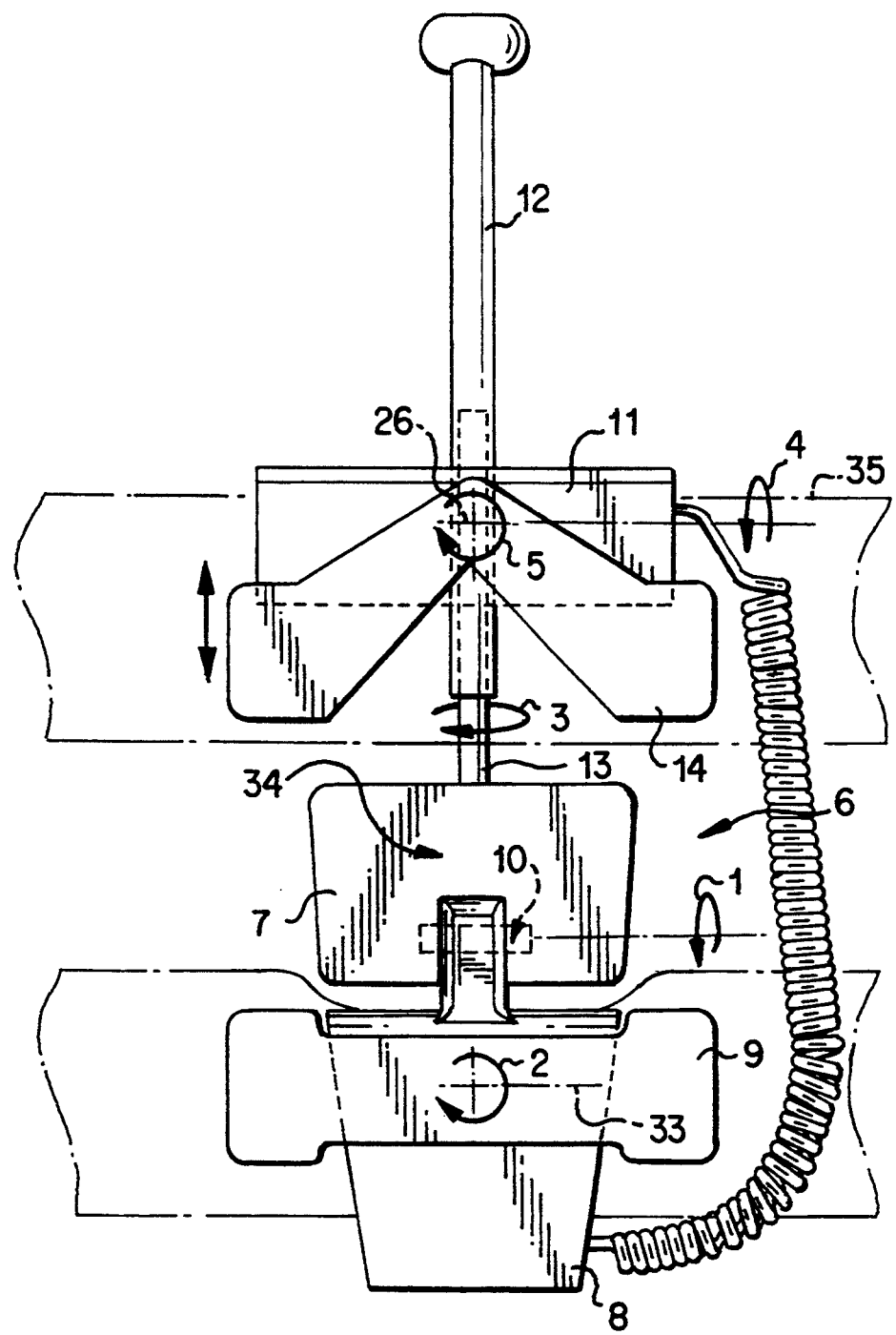
FIG. 2 is a depiction of the device of the present invention showing the five axis of rotation measured.
Figure 3A:
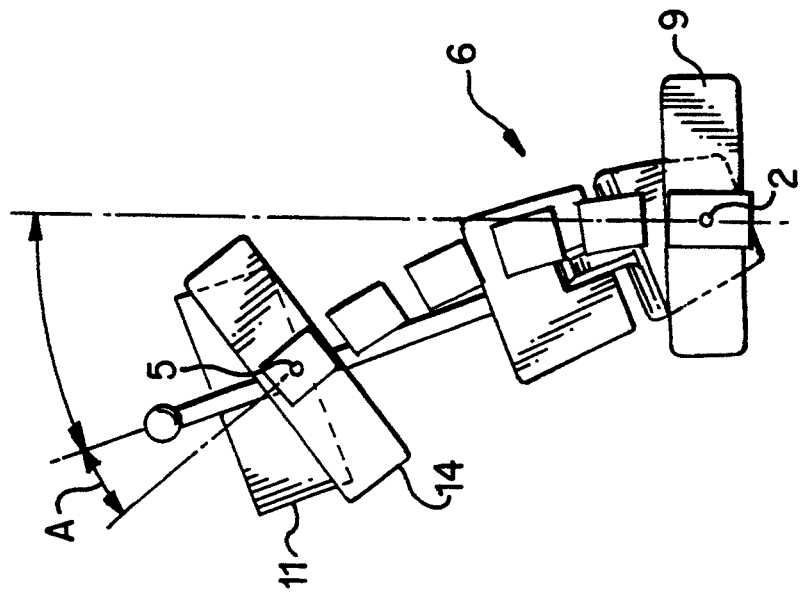
FIG. 3 and FIG. 3A compares rotational motion and measurement using the respective devices of FIG. 1 and 2.
Figure 3:
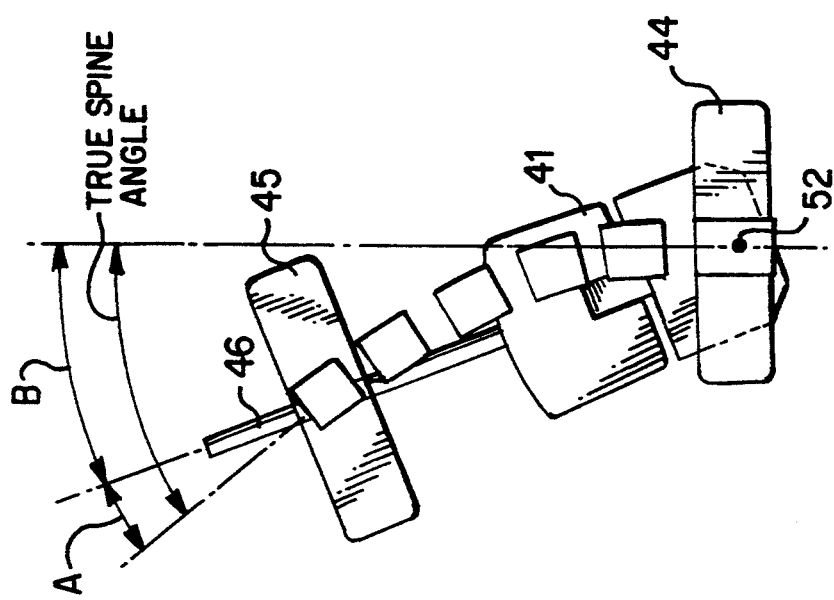

The invention as well as its advantages over the prior art will however, will be more fully appreciated by having reference initially to FIGS. 1 and 2 of the drawings. FIG. 1 is a diagrammatic representation of the device described in U.S. Pat. No. 5,146,929. As shown, articulating inclosure 41 consists of an upper housing 43 and a lower housing 42 which are pivotally connected together. A first plate 44 is pivotally attached to the lower housing and itself attaches to a strap which is adapted to fit around the lower torso of a human subject. A rotatable, elongated shaft 46 connects upper housing 43 with a second plate 45 which is also attached to a strap which fits around the subject at a higher position on the torso. The device accordingly, permits determination of three individual degrees of rotation which are designated 51, 52 and 53 in the drawing.

FIG. 2 of the drawings is a diagrammatic representation of the device of the present invention generally corresponding to the depiction of FIG. 1. As shown in the drawings, first articulating inclosure 6 consists of a housing 8 which is pivotally attached to housing 7. Plate 9 also pivotally attaches to the housing 8 and is itself attached to a belt adapted to fit around the lower torso of the subject. It will be appreciated that with respect to the first articulating inclosure and the attached plate and belt, the structure of the present invention is the same as that of U.S. Pat. No. 5,146,929 illustrated in FIG. 1 of the drawing. A rotatable shaft consisting of telescoping tubes 12 and 13 connects the articulating inclosure 6 with a third housing 11. Pivotally attached to the third housing 11 is a second plate 14 to which a belt also attaches for securing the upper portion of the unit to the upper torso of the subject. Of significance, the device of the present invention, as illustrated in FIG. 2 of the drawings, provides an additional two points of rotation 4 and 5 in addition to points 1, 2, and 3, which are essentially the same as in the device of the prior art.

The significance of the two additional axis of rotation provided by the device of the present invention will best be understood by having reference to FIGS. 3 and 3A, FIGS. 4 and 4A and FIGS. 5 and 5A-D of the drawings which respectively compare the spinal movement measured using the device of the prior art and that of the present invention. As shown for example in FIG. 3 and FIG. 3A; of the drawings, the fifth axis of rotation is determined by measuring rotation at pivot 5 where the second plate 14 pivotally connects with housing 11 and compensates for the difference or last motion A between the true angle of lumbar rotation of the spine and the measured angle B of rotation which is found using the device of the prior art.

Figure 4A:
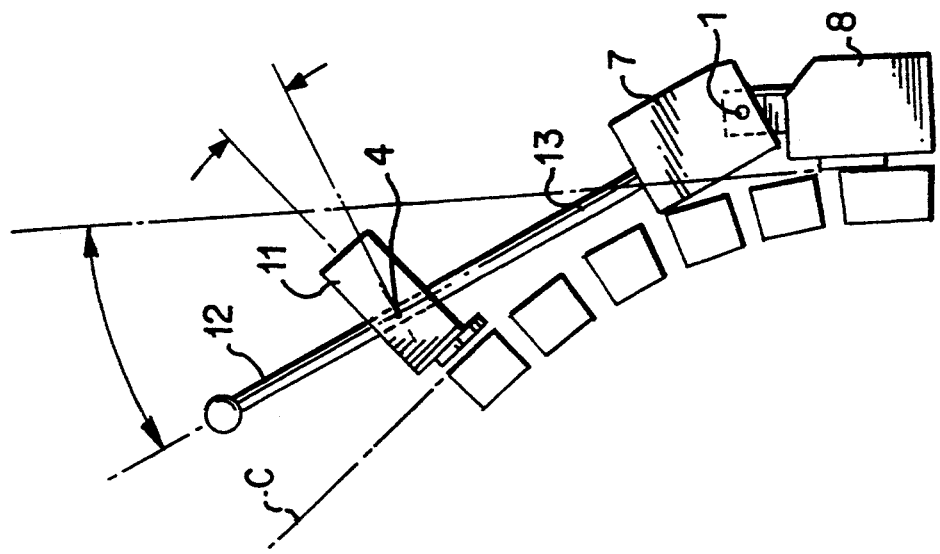
FIG. 4 and FIG. 4A compare tilt motion and measurement using the respective devices of FIG. 1 and 2.
Figure 4:
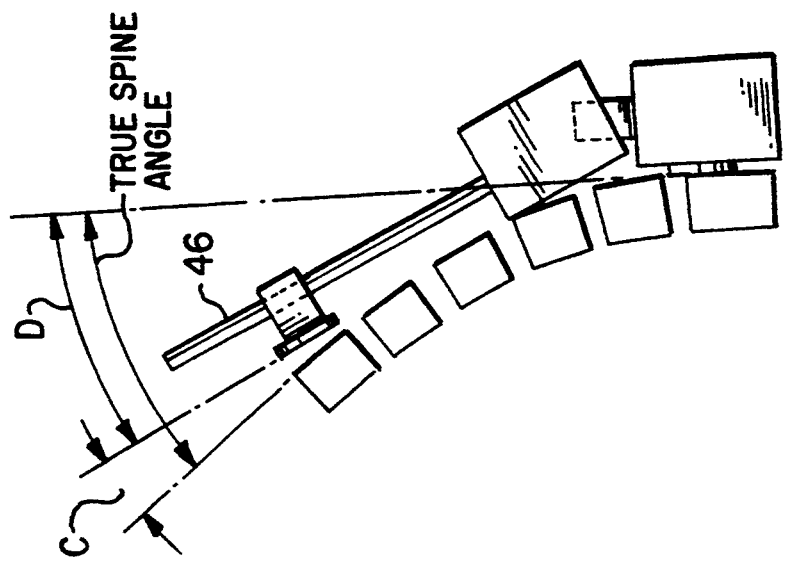
Figure 6A:
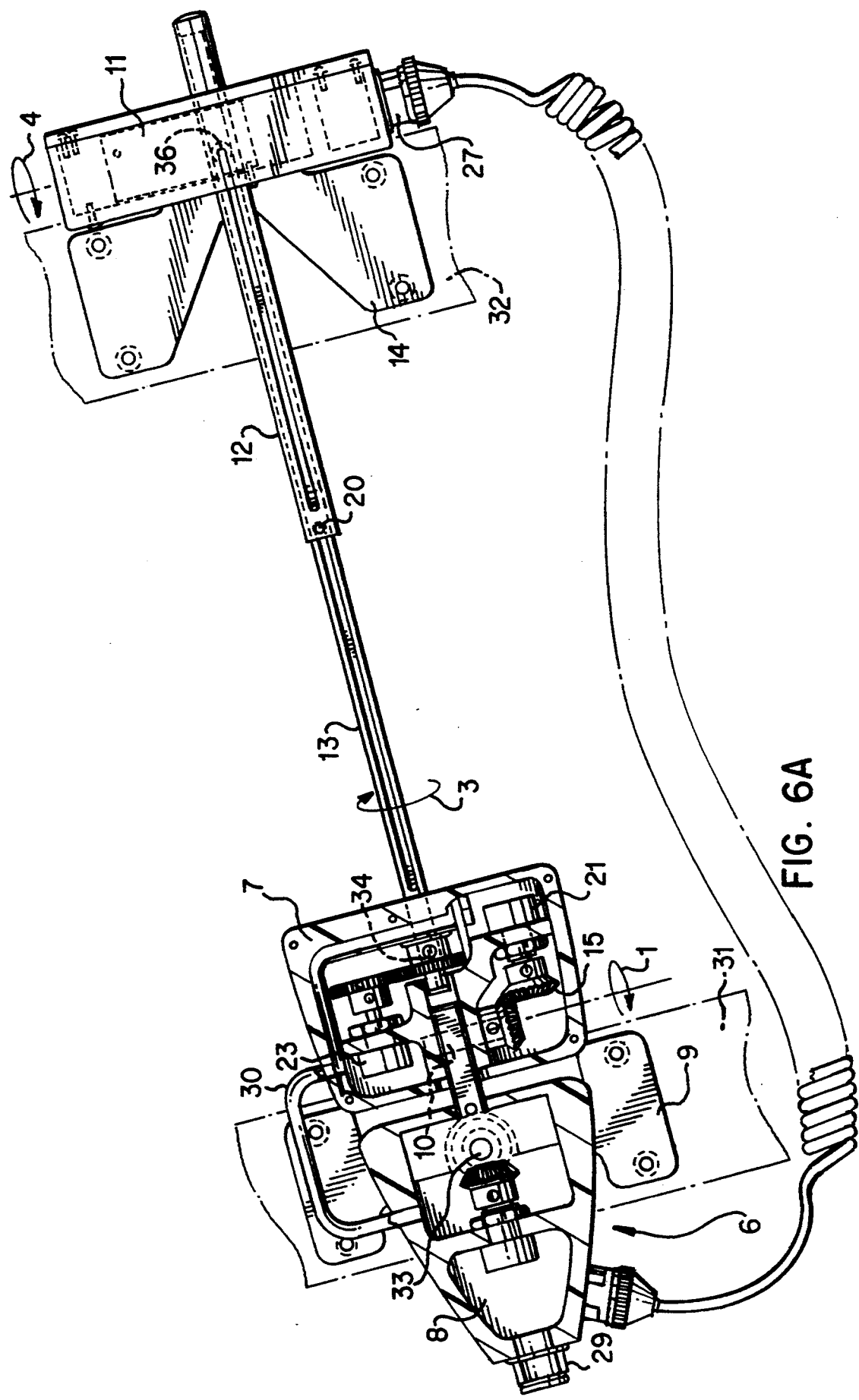
FIGS. 6 A-E are a detailed cut away machine drawing illustrating the components of the device of the present invention.
Figure 6B:
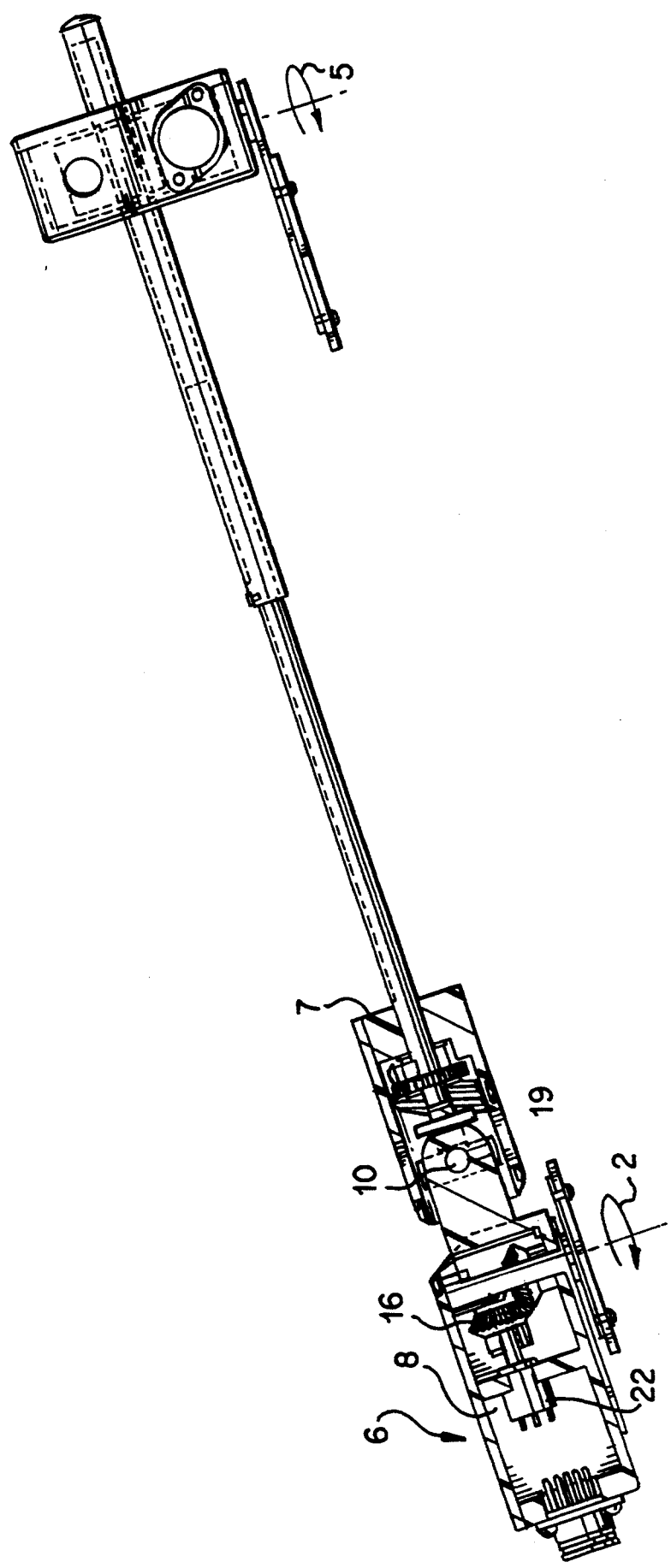
Figure 6C:
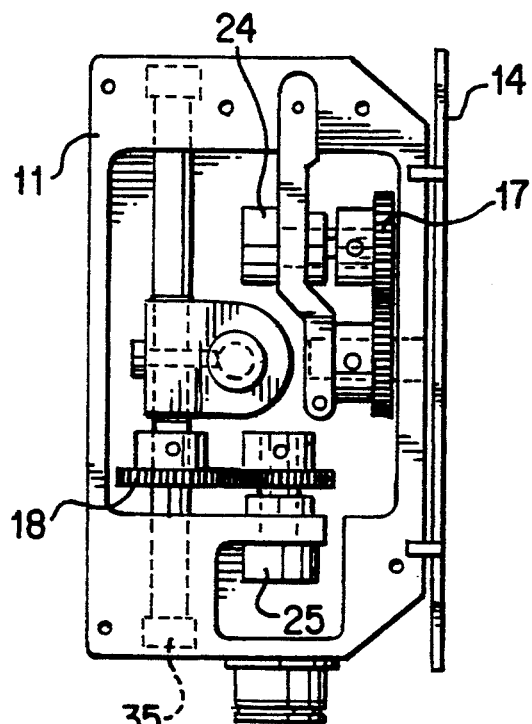
Figure 6D:
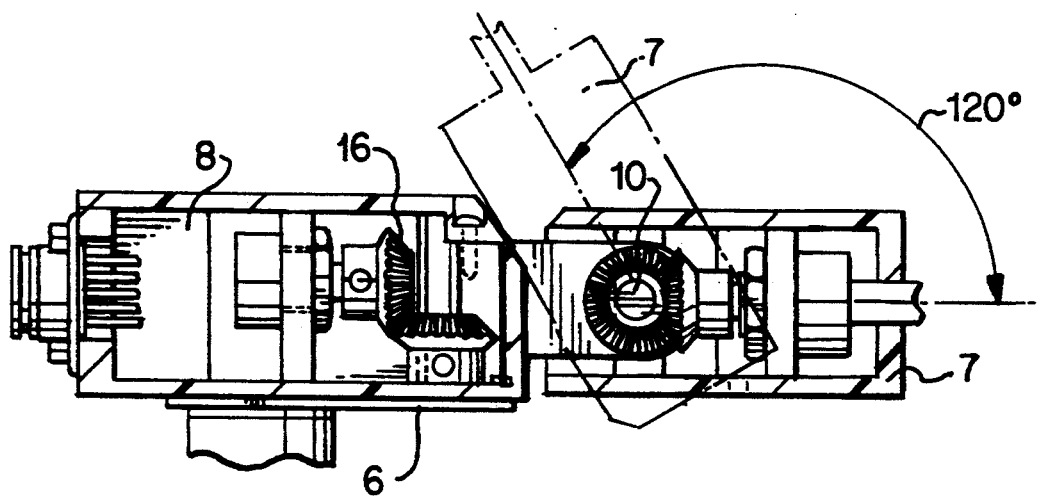
Figure 6E:
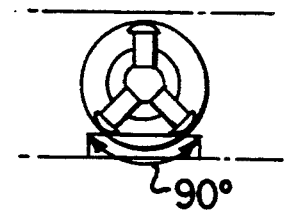

As shown in FIG. 4 and FIG. 4A of the drawings, a similar discrepancy C occurs in the measurement of tilt motion D as measured by axis of rotation 1 in the device of the prior art. By providing an additional axis of rotation 4 in housing 11, compensation for this deviation is achieved.

FIG. 5 and FIGS. 5A-D of the drawings illustrate the manner in which the present invention compensates for the effect of mechanical coupling on rotational movement of the spine by providing additional axis of rotation 5 to compensate for erroneous flexional lateral bending measurements using the device of the prior art.

A complete understanding of the structure of the device of the present invention will however, result from having specific reference to FIG. 6 which consists of detailed cut away views A-E of the device of the present invention in order to illustrate more fully the component elements of the illustrated device. As previously noted, articulating inclosure 6 consists of first housing 8 and second housing 7 which are joined together by first pivot connector 10 which is a shaft. A third housing 11 is remotely connected to the second housing 7 by means of an elongated telescoping shaft consisting of an outer tube 12 and an inner tube 13. Plate 9 is pivotally attached to housing 8 by pivot connection 33. A strap 31 for encircling the waist of the subject and attaching the articulating inclosure to the lower portion of the subjects back is itself is rigidly attached to the plate 9. A second upper plate 14 is pivotally mounted to housing 11 by pivot connector 36 and is also attached to a belt or strap so that the plate 14 can be secured to the subject adjacent to the top of the lumbar spine. A third pivot connector 34 connects the telescoping elongated shaft 12, 13 and the housing 7 about a third axis of rotation 3 which is perpendicular to both the first 1 and second 2 axis of rotation and coextensive with the axis of rotation of the elongated shaft. A fourth pivot connector 35 connects plate 14 and housing 11 about a fourth axis which is perpendicular to the third axis 3. A fifth pivot connector 36 connects the third housing 11 to the elongated shaft 12, 13 about a fifth axis which is perpendicular to both the third 3 and fourth 4 axis. Each pivot connector and corresponding axis of rotation is independently provided with a sensor, which is a potentiometer, for separately measuring the relative pivotally motion of each of the pivots about their respective axis. Potentiometers 24 and 25 respectfully are indirectly driven by spur gears 17 and 18 respectively. Potentiometer 21, which measures rotation around axis 1 is driven indirectly by miter gear 15. Potentiometer 22, which determines rotation around axis 2 is driven by miter gear 16, and potentiometer 23, which measures rotation of the connecting shaft about axis 3 through spur gear 19. Transmission of electric signals produced by the respective potentiometers in reaction to rotational movement is transmitted between the upper housing 11 and lower housing 8 by means of connecting cables (not shown) and four pin electric connectors 26 and 27. Electric connection between the housings 7 and 8 are through connecting tube 30.

Signals from the five sensors which detect rotational movement as described above are directed to external monitoring equipment, not shown, by suitable flexible wire or cable leads which can extend from the three housings containing the sensors but more advantageously extend from a seven pin connector 29 illustrated in FIG. 6 of the drawing.

While it is preferred to utilize analog electrical rotatory potentiometers as the sensors in accordance with present invention. Measurements can also be achieved by use of digital encoders and other transducers which utilize gages, sound, electronic magnetic or optical elements to register the resulting mechanical motions of the members described and to convert them to signals capable of being monitored by recorders, microprocessors, or computers.

As before described, it is preferred in accordance with the present invention that the rotating shaft connecting the articulating enclosure with the third housing 11 be a telescoping shaft whose length can be varied to change the distance between housing 11 and articulating enclosure 6 in accordance with the requirements of the subject be tested. Thus, the two telescoping sections 12 and 13 of the shaft are longitudinally channeled such that rotation of one section of the shaft results in the same rotation of the other section of the shaft. A suitable dowel pin 20 is provided at the terminus of shaft 12 to prevent the two shafts from becoming disengaged.

The device of the present invention is designed to be attached about the lumbosacral joint so that axis 1 is substantially coincidental with the major flexion-extension axis of rotation of the fifth lumbar vertebra and first sacral interspace.

Rigid plate 9 is adapted to be secured against the back of a subject at the base of the lumbar spine with housing 8 vertically aligned under housing 7 and with axis 1 located transversely to the first sacral interspace. This is achieved by strapping plate 9 distally to the superior horizontal aspect of the sacrum and by strapping the plate 14 along the vertically access of the lumbar spine in line with the first lumbar vertebra. Rigid plate 14 is adapted to be secure to the subject adjacent to the top of the lumbar spine. It has the capacities of free linear sliding motion along a supporting shaft to allow for lengthening and shorting of the lumbar spine during the measurement process. As here before described, pivot connection 10 joins the two housings 7 and 8 for relative motion about axis 1. Pivotal motion of housing 7 and 8 about axis 1 corresponds to flexion-extension of the lumbar spine of the subject.

Pivot connection 33 mounts plate 9 to housing 8 about axis 2 which is perpendicular to axis 1. Axis 2 is also spaced distally from axis 1 but they can intersect as well. Relatively pivotally movement between plate 9 and housing 8 corresponds to lateral bending of the subject's lumbar spine.

Pivot connection 3 is provided between shaft 12, 13 and housing 7 about axis 3. Axis 3 is perpendicular to and intersects both axis 1 and axis 2. Pivotal movement between shaft 12, 13 and housing 7 about axis 3 corresponds to axial rotation of the subjects lumbar spine.

Pivot connection 35 joins housing 11 to telescoping shaft 12, 13 for relative motion about axis 4. Pivot connection 36 joins plate 14 to housing 11 for rotation about axis 5.

The device of the invention can be readily fitted upon any subject by simply adjusting the straps that mount it to the subject. Once it has been properly located on the subject's back all further calibration can be carried on electrically on the recording or analyzing equipment utilized with the device.

Locating the device on the back of the user is relatively simply to one familiar with the anatomy of the lumbar region. It can be positioned by locating it relative to the bony anatomy of the subject or can be set at the L5S1 verbal interface by visual location while subject is in a bent position. The upright shaft 12, 13 can be visually alined with the subjects spine which is normally vertical. The encircling straps that frictionally hold the device to the body of the subject will accurately maintain it in place whether the subject is clothed or unclothed. The strap frictionally engages the subject's body or clothing and prevents relative movement between the plates 9 and 14 and the body of the subject.

As illustrated in the accompanying drawings, movement about the five described axis of rotation, in accordance with the invention, is transmitted by appropriate gears or directly to individual potentiometers which produce electrical signals in response to the rotational motion around each axis. While a convenient and advantages means for accurately measuring and recording the five rotational movements is thereby provided, it will be apparent to those of ordinary skill in the art, that other means than those described herein and in U.S. Pat. 5,146,929 can also be employed to quantitatively measure and register these movements.

What is claimed is:

1. An apparatus for measuring motion of the lumbar spine of a subject about five axes, comprising:
   an articulating enclosure including first and second housing and a third housing remotely connected to said second housing by a connecting means;
   first pivot means joining said first and second housings for relative motion about a first, horizontal axis;
   first plate means pivotally mounted to the first housing;
   said first plate means being adapted to be secured to the back of a subject at the base of the lumbar spine with the first housing vertically aligned under the second and third housing and with the first axis located transversely across the lumbar spine;
   second plate means pivotally mounted to the third housing;
   the second plate means being adapted to be secured to the subject adjacent to the top of the lumbar spine;
   second pivot means operably mounting said first plate means to the first housing about a second horizontal axis that is perpendicular to the first horizontal axis;
   third pivot means operably connecting said connecting means and second housing about a third vertical axis which is perpendicular to both said first and second axis, and coextensive with said connecting means;
   fourth pivot means operably connecting said second plate means and said third housing about a fourth horizontal axis which is parallel to said first axis;
   fifth pivot means operably connecting said third housing to said connecting means about a fifth horizontal axis which is parallel to said second horizontal axis;
   a plurality of sensing means each responsive respectively to relative pivotal motion of each of said pivot means about their respective axis; and means for receiving and transmitting to a register, signals produced by said sensing means in response to said pivotal motion.

2. The apparatus of claim 1 wherein said connecting means telescopes.

3. The apparatus of claim 1 wherein said sensing means are potentiometers which produce electric signals in response to rotational motion imparted thereto from said pivot means.

4. The apparatus of claim 1 wherein said first and second plate means are secured to said subject each by a strap which encircles the subject laterally.

5. The apparatus 1 wherein said connecting means is an elongated shaft.

6. In an apparatus for independently measuring lumbar spinal movement which includes separate means for respectively registering lumbar flexion/extension, lateral bending and rotation about three independent axis of rotation, the improvement which comprises: a plurality of additional means for registering rotational movement about additional axis of rotation in response to said lumbar spinal movement to compensate for distorted measurements of said lumbar flexion/extension, lateral bending and rotation induced by interaction thereof during spinal movement.

7. The device of claim 6 wherein said three independent axes of rotation include first and second horizontal axes which are mutually perpendicular and a third vertical axis which is perpendicular to both said first and second axes; and said additional axes of rotation are a forth axis of rotation which is parallel to said first axis and a fifth axis of rotation which is parallel to said second axis, said additional registering means and axes of rotation being disposed at a point in the device to engage the spine higher than said three independent axes.

* * * * *